United States Patent [19]

Meienhofer

[11] 4,108,846

[45] Aug. 22, 1978

[54] SOLID PHASE SYNTHESIS WITH BASE N ALPHA-PROTECTING GROUP CLEAVAGE

[75] Inventor: Johannes Arnold Meienhofer, Upper Montclair, N.J.

[73] Assignee: Hoffmann-La Roche Inc., Nutley, New Jersey 07110

[21] Appl. No.: 764,605

[22] Filed: Feb. 1, 1977

[51] Int. Cl.² .......................................... C07C 103/52
[52] U.S. Cl. ............................................. 260/112.5 R
[58] Field of Search ................................. 260/112.5 R

[56] References Cited

U.S. PATENT DOCUMENTS

| 3,835,175 | 9/1974 | Carpino et al. | 260/112.5 R |
| 3,839,396 | 10/1974 | Otsuka et al. | 260/112.5 R |
| 3,944,538 | 3/1976 | Bodansky | 260/112.5 R |

OTHER PUBLICATIONS

Merrifield, Advances in Enzymology 32, 1969, pp. 221-295.

Primary Examiner—Delbert R. Phillips
Attorney, Agent, or Firm—Samuel L. Welt; George M. Gould

[57] ABSTRACT

An improved solid phase peptide synthesis method is disclosed utilizing base labile Nα-amino acid protecting groups. Such method provides a more efficient synthesis procedure in that it eliminates acid treatment thereby preventing loss of peptide from the support during each deprotection cycle and eliminates a substantial number of wash cycles in each step. A preferred base labile Nα-amino protecting group is the 9-fluorenylmethyloxycarbonyl group (Fmoc) and a preferred base for deprotection is piperidine.

6 Claims, No Drawings

SOLID PHASE SYNTHESIS WITH BASE Nα ALPHA-PROTECTING GROUP CLEAVAGE

BACKGROUND OF THE INVENTION

Solid phase peptide synthesis, the alternative to conventional synthesis in solution, is distinguished by its speed and convenience of operation. Successful applications to the synthesis of a large variety of biologically active peptides and to the commercial production of adrenocorticotropin have been reported. However, it has been widely recognized that the solid phase procedure, in its present state of development, suffers from several shortcomings as formation of truncated and failure sequences and loss of peptide from support, which result, overall, in low yields of heterogeneous peptides that often cannot be completely purified with existing fractionation procedures. Some of the main shortcomings of the procedure originate from the use of acids such as trifluoroactic acid for the removal of the Nα-protecting groups in each cycle, and from the acidolytic removal of the completed peptide from the solid support. Specifically, several side reactions have been identified, such as (1) partial loss of side chain protecting groups during acidolytic cleavage of Nα-protecting groups, (2) loss of peptide from the solid support due to partial cleavage of the anchoring link during acid treatment, and (3) partial destruction of the synthetic product during the commonly used HF cleavage of the final peptide from the resin.

Efforts to minimize undesired side reactions have led to development of more acid-stabile side chain protecting groups and peptide to resin bonds which did, indeed, suppress losses of side chain protection and of peptide from support. However, the acidolytic removal of the completed peptide from the resin and complete protecting group removal became more difficult with these groups.

Complete elimination of acid treatment in solid phase peptide synthesis is thus highly desirable. Such procedure would totally bypass all potential side reactions originating from partial acid sensitivity.

Moreoever, an entire operation would be saved in each cycle and consequently the number of required washing steps could be considerably reduced. Nevertheless, all known procedures and variations of solid phase peptide synthesis are characterized by the use of acidolytic cleavage of Nα-protecting groups in each cycle and elimination of acid treatment has heretofore not been attempted. Base treatment is, of course, employed in all presently used solid phase procedures to deprotonate the ammonium groups after acidolysis of Nα-protecting groups.

DESCRIPTION OF THE INVENTION

The present invention relates to an improved method of conducting solid phase peptide syntheses. Said method involves the use of base labile Nα-amino protecting groups on the initial amino acid covalently coupled to the resin support and on each amino acid which is sequentially added to the growing peptide chain on the resin support. After each coupling step the terminal Nα-amine protecting group is then cleaved by base treatment to provide a free amine group ready for coupling in the next addition cycle.

Suitable base labile Nα-protecting groups which can be used in the present method include the trifluoroacetyl (Tfa), the 9-fluorenylmethyloxycarbonyl (Fmoc), the 4-toluenesulfonylethyloxycarbonyl (Tsoc), the methylsulfonylethyloxycarbonyl (Mesoc), the 2-(triphenylphosphono)-ethyloxycarbonyl (Peoc), the 2-cyano-t-butyloxycarbonyl (Cyoc), and the phthalyl (Pht) groups. Particularly preferred is the Nα-(9-fluorenylmethyloxycarbonyl) protecting group.

The selection of a specific base used to cleave the base labile Nα-amino protecting group is not narrowly critical. Thus organic or inorganic bases may be used. Suitable organic bases include amines, either primary, secondary or tertiary. Examples of suitable amines include cyclohexylamine, 1,5-diazabicyclo [5,4,0] undec-5ene, piperidine ethanolamine, pyrrolidine, diethylamine, morpholine, piperazine, dicyclohexylamine, hydroxylamine, N,N'-isopropylethylamine, N,N,N',N'-tetramethyl 1,8-naphthalenediamine, tributylamine, triethylamine and triethylendiamine.

Inorganic bases include sodium hydroxide and ammonia. The inorganic bases are preferably employed in conjunction with one or more organic solvents. Thus sodium hydroxide is used in the form of Tesser's base, i.e., dioxane-methanol-4N sodium hydroxide and ammonia as a 5 molar solution in methanol-methylene chloride.

Each base may of course interact with the various Nα-amine protecting groups in a varying manner. Thus when the Fmoc group is used as the protecting group most efficient cleavage ($<15$ min) is obtained with piperidine, cyclohexylamine, 1,5-diazabicyclo [5,4,0] undec-5-ene, ethanolamine, pyrrolidine or Tesser's base. Piperidine is a particularly preferred base for cleavage of the Fmoc group.

The cleavage reaction is carried out in an organic solvent conventionally employed in solid phase peptide synthesis. Suitable solvents include the halogenated lower alkyls, preferably chlorinated lower alkyls such as methylene chloride. Room temperature is most conveniently employed for the cleavage reaction.

The concept of omitting acid treatment in solid phase synthesis and of generating free amine groups directly by base treatment can be demonstrated using the Fmoc protecting group. The tetrapeptide Leu-Ala-Gly-Val is a convenient target sequence because it has frequently been used before as a model to demonstrate the feasibility of modified solid phase procedures. Attachment of Fmoc-L-valine to hydroxymethylated copolystyrene 1%-divinylbenzene resin was carried out with the aid of carbonyldiimidazole and resulted in a substitution level of 0.35 mmol Fmoc-Val per gram of resin.

The solid phase synthesis was conducted in a manual apparatus. A cycle for the incorporation of each amino acid into the growing peptide chain involved base cleavage of the Nα-Fmoc groups by 50% piperidine in methylene chloride for 30 min, repeated washings with methylene chloride, and peptide bond formation with the aid of dicyclohexylcarbodiimide (repeated coupling, 2 × 2 hr) with repeated washing operations in between. In this manner Fmoc-Gly-OH, Fmoc-Ala-OH, and Fmoc-Leu-OH were incorporated and the Nα-Fmoc group of the completed tetrapeptide was cleaved as before. Removal of Leu-Ala-Gly-Val from the resin support was carried out in anhydrous liquid HF to provide a crude preparation in 83.8% yield which was purified by ion exchange chromatography on AG 50 W × 2. The purified tetrapeptide, obtained in 58.1% overall yield, was homogeneous by tlc in several solvent systems, ir spectral data, and amino acid analysis. Its optical rotation agreed with literature data.

A solid phase synthesis of the same tetrapeptide but using Nα-t-butyloxycarbonylamino acids was carried out in parallel under conventional conditions. The Nα-protecting groups were cleaved in each cycle by 50% trifluoroacetic acid in methylene chloride. The acidolytic cleavage was followed by deprotonation of the amine groups using 10% triethylamine in methylene chloride in the manner typical for all known procedures of solid phase peptide synthesis. The final overall yield of purified homogeneous tetrapeptide from this otherwise identical synthesis was 40.3%.

This exploratory study establishes that base-labile Nα-protecting groups such as the 9-fluorenylmethyloxycarbonyl group may be used with advantage in solid phase peptide synthesis. Base cleavage is readily obtained within 30 min producing unprotonated amine groups to be immediately condensed with the subsequent amino acid. A tetrapeptide, Leu-Ala-Val-Gly, was prepared by this simplified method in considerably higher yield than that obtained from a regular solid phase procedure and the product was indistinguishable from authentic material. Thus the advantages of the simplified procedure are:

1. Ommission of acid treatment in each cycle
2. Reduced washing and solvent requirements
3. Elimination of loss of side chain protection
4. Elimination of loss of peptide from solid support
5. Can monitor cleavage reaction with U.V.

The following Examples serve to further illustrate the present invention. Melting points are uncorrected. Thin layer chromatography (tlc) was carried out on precoated silica gel plates (Merck, F-254) with the following solvent systems: (A) HCOOH-$H_2O$-sBuOH (13.5:11.5:75), (B) $CHCl_3$-$CH_3OH$-AcOH (95:5:1), (C) nBuOH-AcOH-pyridine-$H_2O$ (15:3:10:12), (D) nBuOH-AcOH-$H_2O$ (4:1:1), (E) nBuOH-AcOH-$H_2O$ (4:1:5), (F) nBuOH-Pyridine-$H_2O$ (2:1:2, upper phase).

EXAMPLE 1

Preparation of 9-Fluorenylmethyloxycarbonylamino acids.

To a solution of L-alanine (1.78g, 20 mmol) in 10% $Na_2CO_3$ (53 ml) was added dropwise (within 50 min) with stirring and ice bath cooling a solution of 9-fluorenylmethyl chloroformate (5.17g, 20 mmol) in dioxane (40 ml). The mixture was stirred for 1 hr at 0° and 15 hr at 5°, poured into $H_2O$ (1.5 liters) and extracted with ether (2 x). The aqueous layer was cooled in an ice bath, acidified with concentrated HCl to pH 2-3 (white precipitate) and extracted with EtOAc (3 × 500 ml). The organic phase was washed with $H_2O$, dried ($MgSO_4$), filtered, and evaporated. Ether-petroleum ether was added to the residue which crystallized while being kept at 5°. The crude product (5.94g, 95.5%) was recrystallized from methanol-petroleum ether to yield colorless crystals of Fmoc-L-alanine (5.61g, 90.2%), mp 144.5°-145.5°; $[\alpha]_D^{25}$ = − 11.7° (c 1, $CH_3OH$); tlc, $R_f$ 0.8 (A), 0.3 (B); uv max ($CH_2Cl_2$) 267 nm (ϵ18,950), 290 (5,280), 301 (6,200).

Analysis: ($C_{18}H_{17}N_1O_4$); Calcd. C 69.44, H 5.50, N 4.50; Found C 69.18, H 5.54, N 4.48.

Lit.: [16] mp 144°-145°, $[\alpha]_D^{25}$ = − 3.48° (c 2.5, EtOAc).

Other Fmoc-amino acids were prepared in essentially the same manner:

Fmoc-glycine:
97%, mp 173°-174°, tlc $R_f$ 0.7 (B).
Lit.: [16] mp 173°-176°.

Fmoc-L-leucine: 87%, mp 152°-153°; $_D^{25}$ = − 7.4 (c 2.5, EtOAc); tle $R_f$ 0.75 (B).
(Lit.: [16] mp 155°-156°; $[\alpha]_D^{28.3}$ = − 4.44° (c 2.5, EtOAc).

Fmoc-L-valine: 91.6%, mp 144°-145°; $[\alpha]_D^{25}$ = + 5.01° o (c 1, EtOAc),
−4.52° (c 1, $CH_3OH$); tlc $R_f$ 0.9 (A), 0.45 (B).

Analysis: ($C_{20}H_{21}N_1O_4$); Calcd. C 70.78, H 6.24, N 4.13; Found C 70.67, H 6.30, N 4.10.

EXAMPLE 2

9-Fluorenylmethyloxycarbonyl-L-valine Resin.

All reagents and glassware were carefully dried, anhydrous distilled solvents were used and moisture was excluded during all manipulations. To a solution of carbonyldiimidazole (649 mg, 4 mmol) in $CH_2Cl_2$ (12 ml) which was stirred and cooled to −5° Fmoc-L-valine (1.358g, 4 mmol) was added at once. The reaction mixture was kept for 30 min at −5° and 30 min at 0°. Hydroxymethyl resin (hydroxymethylated polystyrene-1% divinylbenzene) (2.67g) was added along with $CH_2Cl_2$ (18 ml). The mixture was stirred for 3 days at 25°. The resin was collected by filtration, washed with $CH_2Cl_2$, DMF, $CH_3OH$ (500 ml, each) and dried ($P_2O_5$-KOH) in vacuo. Anal.: N, 0.75%. To block unreacted hydroxyl groups the resin was suspended in $CH_2Cl_2$ (40 ml) cooled to 0° and treated with benzoyl chloride (0.82 ml, 7 mmol) in pyridine (0.68 ml, 8,4 mmol). The mixture was kept for 15 min at 0°. The collected resin was washed with $CH_2Cl_2$, DMF, and $CH_3OH$ (500 ml, each) and dried ($P_2O_5$-KOH) in vacuo for 15 hr at 25° to yield 2.81g of Fmoc-L-valine resin. Analysis showed 0.62% N, corresponding to a substitution level of 0.44 mequiv per gram.

EXAMPLE 3

L-Leucyl-L-alanyl-glycyl-L-valine Resin.

A. By Simplified Solid Phase Synthesis Without any Acid Treatment

Fmoc-L-valine resin (1g, 0.35 mequiv) was placed into a reactor vessel and swelled overnight in $CH_2Cl_2$ (10 ml) and washed several times with $CH_2Cl_2$. During the synthesis 12 ml of solvent per gram of resin was used for each washing and 10 ml per gram for reactions. A cycle for the incorporation of each amino acid into the growing peptide chain involved the following washing and reaction steps:

(1) 50% piperidine in $CH_2Cl_2$ (1 × 2 min, 1 × 28 min)
(2) washing with $CH_2Cl_2$ (6 × 2 min)
(3) Fmoc-amino acid (4 equiv) in DMF—$CH_2Cl_2$ (1:5, 5 ml) (1 × 5 min)
(4) DCCI (4 equiv) in $CH_2Cl_2$ (4 ml) added (1 × 2 hr)
(5) washing with $CH_2Cl_2$, DMF, $CH_3OH$, $CH_2Cl_2$ (3 × 2 min, each)
(6) Fmoc-amino acid (2 equiv) in DMF—$CH_2Cl_2$ (1:5, 5 ml) (1 × 5 min)
(7) DCCI (2 equiv) in $CH_2Cl_2$ (4 ml) added (1 × 2 hr)
(8) washing with $CH_2Cl_2$, DMF, $CH_3OH$, $CH_2Cl_2$ (3 × 2 min, each)

The extent of protecting group cleavage was readily determined in each cycle by totaling the extinction of the released fluorenylmethylpiperidine, at 267 mm, in the filtrates of step (1) and the first 2 washing filtrates of step (2). The completeness of coupling reactions was monitored by the Kaiser ninhydrin (E. Kaiser, R. L. Colescott, C. D. Bossinger and P. I. Cook, Anal. Biochem., 34, 595 (1970)) and the fluorescamine (A. M.

Felix and H. H. Jimenez, Anal. Biochem., 52, 377–381 (1973)) tests. After the completion of the protected tetrapeptide the Nα-Fmoc group was cleaved by applying above steps (1) and (2). The peptide resin was removed from the reaction vessel, thoroughly washed with $CH_3OH$ and $CH_2Cl_2$ and dried in vacuo ($P_2O_5$ and KOH), to yield 1.0 g. Amino acid analysis (concentrated HCl—dioxane (1:1), 110°, 48 hr) showed relative ratios of Gly 0.98, Ala 1.00, Val 1.06, Leu 1.05.

B. By Common Solid Phase Synthesis Using Acidolysis of Nα-Protecting Groups in Each Cycle.

Boc-L-valine resin (700 mg, 0.2 m equiv) was placed into a reactor vessel and swelled overnight in $CH_2Cl_2$ (10 ml). During the synthesis 12 ml of solvent per gram of resin was used for each washing and 10 ml per gram for reactions. A cycle for the incorporation of each amino acid involved:

| | | |
|---|---|---|
| (1) | washing with $CH_2Cl_2$ | (6 × 2 min) |
| (2) | 50% $CF_3COOH$ in $CH_2Cl_2$ | (1 × 2 min, 1 × 28 min) |
| (3) | washing with $CH_2Cl_2$ | (6 × 2 min) |
| (4) | washing with DMF | (6 × 2 min) |
| (5) | 10% $NEt_3$ in DMF | (2 × 2 min, 1 × 10 min) |
| (6) | washing with DMF | (6 × 2 min) |
| (7) | washing with $CH_2Cl_2$ | (6 × 2 min) |
| (8) | Boc-amino acid (4 equiv) in $CH_2Cl_2$ (4 ml) | (1 × 5 min) |
| (9) | DCCI (4 equiv) in $CH_2Cl_2$ (3 ml) added | (1 × 2 hr) |
| (10) | washing with $CH_2Cl_2$, DMF, $CH_3OH$, $CHCl_2$ | (3 × 2 min, each) |
| (11) | Boc-amino acid (2 equiv) in $CH_2Cl_2$ (4 ml) | (1 × 5 min) |
| (12) | DCCI (2 equiv) in $CH_2Cl_2$ (3 ml) added | (1 × 2 hr) |
| (13) | washing with $CH_2Cl_2$, DMF, $CH_3OH$, $CH_2Cl_2$ | (3 × 2 min, each) |

The completed Boc-tetrapeptide resin was subjected to steps (1) and (2) to cleave the Boc group and worked up as described for (A) to yield 707 mg of peptide resin. Amino acid analysis: Gly 1.05, Ala 1.00, Val 1.12, Leu 1.05.

EXAMPLE 4

L-Leucyl-L-alanyl-glycyl-L-valine.

Both peptide resins were processed in essentially the same manner. Treatment with anhyd HF (6 ml) for 1 hr at 0°, evaporation, extraction of the residues with 10% AcOH (3 × 8 ml) and glacial acetic acid (3 × 8 ml) followed by lyophilization afforded crude tetrapeptides which were purified by ion exchange chromatography on an AG 50 W × 2 (200-400 mesh) column (2.4 × 90 cm) using 0.1 M pyridine acetate buffer, pH 4.0 as an eluant at flow rates of 55.3 to 57.9 ml/hr. Fractions containing 5.35 ml were collected and monitored by tlc (solvent system C) with the aid of fluorescamine staining. The fractions containing the main peak material (Nos 147–230) were collected and evaporated, dissolved in EtOH (0.5-1 ml), filtered and precipitated by the addition of anhyd ether. The precipitates were collected by filtration, washed with ether, and dried in vacuo ($P_2O_5$ and KOH), to afford off-white powders.

The yields of products obtained in this manner and their physicochemical data are listed in Table I.

Table I

| | Peptide Resin Amount used, mg | Crude Peptide | | Purified Peptide | | | | |
|---|---|---|---|---|---|---|---|---|
| Solid Phase Procedure | | Amount from HF mg (%)[a] | Amino Acid Analysis[b] | Amount mg (%)[a] | tlc $R_f$(System) | Amino Acid Analysis[b] | Anal $C_{16}H_{30}N_4O_5$ acetate | $[\alpha]_D^{25}$ (c 0.55, EtOH)[c] |
| (A) Nα-Fmoc Base Cleavage (Simplified) | 854 | 90.7 (84%) | Gly 0.99 Ala 1.00 Val 0.98 Leu 1.01 | 62.9 (58%) | 0.71 (C) 0.55 (D) 0.45 (E) 0.48 (F) | Gly 1.01 Ala 1.00 Val 1.02 Leu 1.08 | C, H, N* | +23.3° |
| (B) Nα-Boc Acid Cleavage (Common) | 606 | 50.1 (82%) | Gly 1.15 Ala 1.00 Val 1.15 Leu 0.99 | 24.6 (40%) | 0.71 (C) 0.55 (D) 0.45 (E) 0.48 (F) | Gly 1.03 Ala 1.00 Val 1.02 Leu 1.09 | — | +23.6° |

[a]Percent yield based on substitution level of starting Fmoc-Val-resin, Boc-Val-resin.
[b]Relative ratios (Ala = 1.00) obtained after hydrolysis [conc HCl—dioxane (1:1), 110°, 48 hr].
[c]Lit.:[36] $[\alpha]_D$ = + 23.7° (c 0.85, EtOH); Lit.:[37] $[\alpha]_D$ = + 23.6 (c 0.15, EtOH); + 24.5° (c 0.68).
*L-Leucyl-L-alanyl-glycyl-L-valine × $CH_3COOH$
$C_{18}H_{34}N_4O_7$ Calcd. C 51.60, H. 8.10, N 13.37 Found C 51.70, H 7.73, N 13.43

I claim:

1. In the solid phase synthesis of peptides wherein a first Nα-amino protected amino acid is covalently coupled to a solid phase peptide synthesis resin the Nα-amino protecting group is cleaved off and the resulting free amino group is coupled via peptide linkage to the carboxyl group of a second Nα-amino protected amino acid and the cycle repeated until the desired peptide sequence has been obtained and then said peptide is cleaved from said resin, the improvement comprising using base labile Nα-amino protecting groups on each of said amino acids and using base to cleave said protecting groups in each cycle.

2. The improved synthesis of claim 1 wherein said Nα-amino protecting group is selected from trifluoroacetyl (Tfa), 9-fluorenylmethyloxycarbonyl (Fmoc), 4-toluenesulfonylethyloxycarbonyl (Tsoc), methylsulfonylethyloxycarbonyl (Mesoc), 2-(triphenylphosphono) ethyloxycarbonyl (Peoc), 2-cyano-t-butyloxycarbonyl (Cyoc) and phthalyl (Pht).

3. The improved synthesis of claim 2 wherein said Nα-amino protecting group is 9-fluorenylmethyloxycarbonyl.

4. The improved synthesis of claim 1 wherein said base comprises an organic amine.

5. The improved synthesis of claim 4 wherein said organic amine base is selected from piperidine, cyclohexylamine, 1,5-diazabicyclo [5,4,0] undec-5-ene, ethanolamine and pyrrolidine.

6. The improved synthesis of claim 5 wherein said organic amine base is piperidine.

* * * * *